United States Patent [19]

Michaelson et al.

[11] Patent Number: 4,714,788

[45] Date of Patent: Dec. 22, 1987

[54] TERTIARY OLEFIN PROCESS

[75] Inventors: Robert C. Michaelson, Kinnelon, N.J.; Jeffrey S. Plotkin, Monsey, N.Y.

[73] Assignee: Exxon Chemical Patents Inc., Linden, N.J.

[21] Appl. No.: 885,528

[22] Filed: Jul. 14, 1986

[51] Int. Cl.$^4$ .................... C07C 41/06; C07C 41/44
[52] U.S. Cl. .................. 568/697; 568/699; 568/671; 568/907; 585/324
[58] Field of Search ............ 568/697, 671, 699, 907; 585/324

[56] References Cited
U.S. PATENT DOCUMENTS 4,152,351 5/1979 Drake .................. 568/671

Primary Examiner—Howard T. Mars
Attorney, Agent, or Firm—E. T. Wheelock

[57] ABSTRACT

In a process for separating $C^4$ to $C^7$ tertiary mono-olefins(s) present in a $C^4$ to $C^7$ hydrocarbon mixture containing diolefins which comprises selectively reacting said tertiary mono-olefin mixture with a primary alcohol in the presence of an acid catalyst to convert it to tertiary ether(s), separating the tertiary ether(s) from the unreacted hydrocarbon mixture and containing said tertiary ether(s) in the presence of a catalyst to decompose it to tertiary olefin(s) and a primary alcohol, the improvement which comprises hydrogenating the tertiary ether(s) after it has been separated from the unreacted hydrocarbon mixture and prior to decomposition to saturate the unsaturated ether(s) formed from the diolefins present in the hydrocarbon mixture.

12 Claims, No Drawings

TERTIARY OLEFIN PROCESS

FIELD OF THE INVENTION

This invention relates to an improvement in the industrial process for extracting tertiary olefins from streams also containing other olefins and diolefins in which such stream is reacted with methanol to preferentially convert the tertiary olefins to methyl ethers, the methyl ethers are separated by distillation and the separated methyl ether stream is then decomposed over an acid catalyst to recover the pure tertiary olefins. More particularly it relates to the improvement of hydrogenating the separated methyl ether stream prior to decomposition to convert unsaturated ethers produced from diolefins to saturated ethers. The invention also relates to preferred catalysts and conditions used for such hydrogenation.

BACKGROUND OF THE INVENTION

The extraction of iso-olefins is accomplished industrially by exploiting the preferential reactivity of iso-olefins with methanol to form the corresponding methyl ether compounds. After the ethers are isolated by distillation, the pure iso-olefin can be regenerated by decomposition of the ether over acid catalysts at elevated temperature. For example, isobutylene can be extracted from mixed $C_4$ streams by preferential formation of methyl tertiary butyl ether (MTBE), distilling off the remaining light $C_4$ materials, and finally cracking the MTBE back to methanol and isobutylene. Similarly, isoamylene can be extracted from $C_5$ streams by formation of tertiary amyl methyl ether followed by distillation and crackback.

In each of the above examples the presence of diolefins in the mixed streams causes operational problems. Diolefins as well as olefins are produced in steam cracking and/or coking and are often present in small quantities in the mixed stream after removal of the majority of the diolefins in prior processing, e.g., DMF (dimethylformamide) extraction. Such diolefins also readily react with methanol resulting in methyl ether compounds containing one double bond (unsaturated ethers). Methyl ether streams containing even low levels of unsaturated ether will cause rapid fouling of the ether decomposition catalyst. Typically, this problem is solved by selective hydrogenation of the dienes before the stream enters the etherification reactor.

This approach has several drawbacks. Foremost, over-hydrogenation must be avoided. This is not easily accomplished since there are normally very low levels of dienes (1–3%) in the presence of mono-olefins. Over-hydrogenation would not only lead to loss of desired mono-olefin product and hydrogen but, inasmuch as hydrogenations are exothermic, this situation is a potentially very dangerous one. Additionally, $C_4$ or $C_5$ olefin streams usually contain relatively large amounts of mercaptans. Mercaptans are known noble metal catalyst poisons. All of these factors combined necessitate that a very selective and rugged hydrogenation catalyst be employed. Lastly, treatment of the dienes at this stage requires that the entire olefin containing stream pass through the hydrogenation reactor. This requires the use of a very large and therefore expensive reactor.

SUMMARY OF THE INVENTION

This invention describes an alternate method of handling the operating difficulties arising from the presence of dienes in the olefin stream. According to the invention, in lieu of hydrogenating the dienes or of accepting the fouling of the ether decomposition catalyst, the dienes are allowed to react with methanol along with the iso-olefins and the resulting unsaturated ether after distilling off the light, unreacted olefins is then hydrogenated. This alleviates the safety concern about generating too much heat and a possible run-away reaction. Also, no over-hydrogenation means no loss of product and efficient use of hydrogen. Furthermore, since all of the unreacted olefins have been distilled away, the volume of product entering the hydrogenation reactor is substantially less: this allows a much smaller and consequently much less expensive reactor. Lastly, it has now been discovered that the mercaptan level in the ether product is greatly reduced as compared to the levels found in the crude mixed olefin stream. This allows the use of commercially available unmodified noble-metal catalyst.

DETAILED DESCRIPTION OF THE INVENTION

The hydrogenation step of the present invention is conducted at temperatures of about 40° C. to 200° C., preferably 50° C. to 180° C., in the presence of about 1.0 to 2.0, preferably 1.0 to 1.3 mols, of hydrogen per mole of unsaturation present in the feed. The reaction is carried out at a spatial velocity, as expressed in terms of volume of liquid per volume of catalyst per hour (LHSV), of about 0.5 LHSV to 4.0 LHSV, preferably 1.0 LHSV to 3.0 LHSV. The hydrogenation may be carried out in the vapor or liquid phase, preferably in the liquid phase, at pressures of about 200 psig to 500 psig, preferably 250 psig to 350 psig.

Preferably the water content of the feed to the hydrogenation step is kept below 1000 ppm, more preferably below 50 ppm. This is desirable to mitigate the undesirable byproduct formation of ketones and aldehydes. The chemistry of such by product formation is as follows: unsaturated ethers, i.e.:

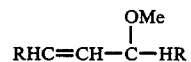

are hydroisomerized over the catalyst to vinyl ethers, i.e.:

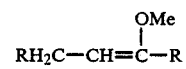

These vinyl ethers are more difficult to hydrogenate than unsaturated ethers and furthermore are easily hydrolyzed to ketones or aldehydes, i.e.:

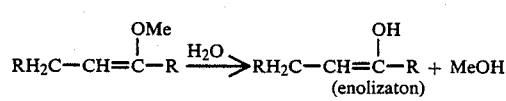

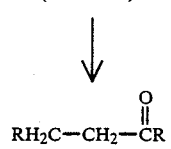

If water is kept out, vinyl ethers can be hydrogenated: otherwise they are partially converted to ketones or aldehydes.

Any hydrogenation catalyst may be used. However, preferred catalysts are the noble metal catalysts belonging to group VIII of the periodic table which are conventional for use for catalytic hydrogenations, as well as their oxides, with or without a carrier material, for example active carbon or alumina. Preferred catalysts are palladium and platinum. A suitable catalyst which does not belong to said group is in particular Raney-nickel. The catalysts are used in usual amounts, preferably in an amount of from about 0.005 to about 0.2% by weight (metal), calculated on the starting compound to be hydrogenated.

In the case of supported catalysts, preferred supports are aluminas having surface areas of 1.0 to 200 m$^2$/gm, preferably 2.0 to 150 m$^2$/g. Preferred aluminas are aluminas of low silica content, preferably below 1% silica contents to reduce acidity and isomerization. The amount of metal dispersed on the catalyst is preferably 0.1 to 1.0 weight percent, more preferably 0.1 to 0.5 weight percent.

Particularly preferred catalysts are IFP LD-265 0.3% Pd on alumina catalyst, UCI G-68 0.1% Pd on alumina catalyst and most preferably Calsicat E-144 SDU 0.5% Pd on alumina catalyst.

In the first step of the etherification process of the present invention, addition takes place easily between the tertiary olefin and the primary alcohol in the presence of a small amount of acid catalyst to give the tertiary ether.

The resultant tertiary ether differs from the components of the starting hydrocarbon mixtures in boiling point and, therefore, can be easily separated by conventional methods such as distillation, etc. Monoolefins other than tertiary olefins can be separated in substantially the same manner as the inert saturated hydrocarbons since they are remarkably low in reaction rate with primary alcohol.

The separated tertiary ether can be completely decomposed to tertiary olefin and primary alcohol by contact e.g., with a solid catalyst consisting of various metal sulfates in the vapor phase.

Thus, in the separation process of the present invention it is not necessary to use expensive apparatus, since both reactions can be performed under mild conditions. Further, since side reactions occur only slightly in both reaction, the separation process has the advantage that yield is high and the quality of the product is excellent.

The etherification step of the present invention can be performed by any known method. For example, when hydrocarbon mixtures containing a tertiary olefin and a primary alcohol are heated at a temperature of about 70° to 150° C. under pressure sufficient to maintain liquid phase in the presence of a small amount of acid catalyst, the tertiary olefin is converted to a tertiary ether in good yield. An acid catalyst can be used in the etherification, such as a mineral acid, for example sulfuric acid, phosphoric acid, hydrochloric acid, etc., an organic sulfonic acid, such as benzene sulfonic acid, para-toluenesulfonic acid, etc., Friedel-Craft catalysts such as cuprous chloride, ferrous chloride, etc., an ion-exchange resin in hydrogen form, or the like.

In view of the reaction rate of the tertiary olefin, use of the liquid phase is preferable. Although, as a primary alcohol suitable for the etherification, any $C_1$ to $C_4$ alcohol can be used, an alcohol which possesses a large difference in boiling point from that of the tertiary olefin to be finally separated, is most suitable. For example, methanol and ethanol are suitable for separating isobutylene present in a $C_4$ fraction or isoamylene, present in a $C_5$ fraction. In the former case, isobutylene is converted either to tertiary butyl methyl ether or tertiary butyl ethyl ether, the boiling points of which are 55° C. and 73° C., respectively, and each of the tertiary ethers formed are separated easily, since the difference in boiling point between the ether and unreacted $C_4$ mixture is great. Similarly isoamylene is converted either to tertiary amyl methyl ether or tertiary amyl ethyl ether, the boiling points of which are 86° C. and 101° C., respectively, and again these are separated easily due to the difference in boiling points from the unreacted $C_5$ mixture.

After the tertiary ether is separated from the unreacted hydrocarbon mixture, the ether is contacted with the above-mentioned solid hydrogenation catalyst as above-described.

Following hydrogenation to saturate the unsaturated ethers present, the hydrogenated product is contacted with any of the well-known ether decomposition catalysts to decompose the product back to the tertiary olefin and the primary alcohol. Such catalysts include metal sulfate catalysts, aluminum compounds supported on silica or other carriers, modified cation exchange resin catalysts, etc. Suitable reaction conditions for the decomposition step are temperature of 100°–250° C. and spatial velocities, as expressed in terms of volume of liquid per volume of catalyst per hour (LHSV) ranging between 0.5 and 30. Conditions are also preferably chosen to maintain conversions of the tertiary ether above 80%. The present invention will be illustrated in more detail with reference to the following examples, which are not however to be interpreted as limiting the scope of the invention.

A number of preferred hydrogenation catalysts were tested under preferred reaction conditions in the hydrogenation of unsaturated ethers in accordance with the present invention.

The laboratory equipment utilized was a ½" O.D. (0.41" ID) 18" long stainless steel reactor. Heat was supplied by circulating hot oil through a jacket surrounding the reactor. Feed was supplied by a high pressure pump and hydrogen was mixed with the feed prior to the reactor inlet and was controlled by a mass flow controller.

The reactor was operated in the upflow mode and the reactor pressure was controlled by a back pressure regulator. In a typical run 30 cc of catalyst was used and it was held in place by glass wool plugs.

The reactor effluent was cooled, degassed and collected for analysis by capillary gas chromatagraphy. The gasoeus effluent from the reactor was measured by a wet test meter and the data was used to perform material balance calculations.

RESULTS

The hydrogenations were conducted in the liquid phase over solid palladium on alumina catalysts. The pressure ranges looked at were 200–450 psig while the temperatures ranged from 40°–200° C. LHSV's of 0.3 to 4.0 were also looked at. The hydrogen, in most cases, was maintained at 20% molar excess based on the mole percent unsaturation present in the feed.

The TAME feedstock used in all the experiments was produced from an actual isoamylene containing cat cracker stream by reacting it with 50 weight percent methanol at a temperature of 50° C. for 6 hours in the presence of an acid catalyst and should be representative of what would be found in a commercial plant with the following exceptions. The TAME does not contain any heavy isoprene ether or ethers of cyclopentadiene. This is because the laboratory distillation of the TAME to separate the unreacted hydrocarbons was so efficient that the heavy isoprene ether and cyclopentadiene ethers went bottoms. To test the hydrogenation of the heavy isoprene ether it was added to the TAME in one of the runs. This is noted in the table below. The sulfur level of the TAME was 10 ppm. The level of sulfur in a commercial feed might be near 50 ppm (40 ppm thiophene, 10 ppm mercaptans). This difference should not change the performance of the catalyst since analysis of the feed and product shows the same level of sulfur. This indicates that the types of compounds containing the sulfur do not have a high affinity for the catalyst. Three different 15 gallon barrels of TAME were used, each containing slightly different amounts of unsaturated ethers. The TAME and unsaturated ether composition of each barrel is given below.

TAME Feed Analysis

| Component | wt % | | |
|---|---|---|---|
| | Barrel 1 | Barrel 2 | Barrel 3 |
| TAME | 96.3 | 92.47 | 94.447 |
| Light Isoprene Ethers | 0.594 | 0.299 | 0.347 |
| Piperylene Ethers | .721 | 2.818 | 2.674 |

IFP LD-265 (EFFECT OF DRYING FEED)

The first catalyst tested was IFP LD-265. This catalyst contains 0.3% palladium dispersed on alumina. The catalyst is manufactured in 2-4 mm spheres; however, to pack the laboratory scale half inch reactor, it was necessay to crush and sieve the spheres to 12-16 mesh.

The catalyst as received is in an oxidized form. For use as a hydrogenation catalyst the palladium oxide was first reduced to Pd° by flowing pure hydrogen (100 ml/min) over it at 80° C. for 16 hours.

The results obtained with this catalyst are given in Table 1 below. In the first three runs the pressure was 300 psig and the LHSV was 2, and in run 12560-42015 the pressure was 450 psig and the LHSV 2.5

TABLE 1

| Exp. No. | Water ppm | T °C. | Select to Satd. Pip Ether | Select to Vinyl Ether | Select to 2-Pentanone |
|---|---|---|---|---|---|
| 12560-11-106 | 5000 | 80 | 31.5 | 64.2 | 3.6 |
| 12560-11-106 | 100-200 | 114 | 40.4 | 53.9 | 4.9 |
| 12560-42-6 | 100-200 | 100 | 83.0 | 11.4 | 7.4 |
| 12560-42015 | 100-200 | 100 | 74.5 | 14.4 | 6.7 |

As can be seen when the feed is dry, i.e., 100-200 ppm water, selectivity to desired saturated piperylene ethers is greatly increased and selectivity to undesired vinyl ether is decreased. Selectivity is poor even with dry feeds if the catalyst has been previously exposed to wet feeds which was the case with respect to Run 12560-11-106. In Run 12560-420 15 the feed was spiked with 0.6 weight percent heavy isoprene ether added. The product from this run was analyzed and it was found that 100% of the heavy isoprene ether had been hydrogenated. This shows that both light and heavy unsaturated isoprene ether isomers will smoothly hydrogenate to the expected saturated products.

Calsicat E-144 SDU, 0.5% Pd/alumina, 8×14 mesh spheres (#73C-080C) was loaded into the reactor (30 cc/25.05 g). The catalyst was activated by flowing pure hydrogen (100 ml/min) over it at 80° C. for 16 hours. A range of operating temperatures and LHSV's were explored. In all these experiments the pressure was kept constant at 300 psig and the hydrogen flow was maintained at 20% molar excess based on the mole percent unsaturation in the TAME feedstock. The screening results are given in Table 2 below.

The effect of temperature upon conversion and selectivity can be seen from the runs shown below. Also, the better performance of Calsicat E-144 SDU as compared to IFP LD-265 and UCI G-68E catalysts screened can also be seen. UCI G-68 catalyst is a 0.1% Pd on alumina selective hydrogenation catalyst with a very low surface areas support (2-5 m²/gram).

TABLE 2

| Run No. | Catalyst | Temperature | Light Isoprene Ether Conv. | Piper. Ether Conv. | Selectivity | | | |
|---|---|---|---|---|---|---|---|---|
| | | | | | Sat. Piper. Ether | Vinyl Ethers | 2-Pentanone | Ketal |
| 13203-22 | Calsicat E-144 SDU | 40 | 100 | 93.0 | 87.9 | 14.0 | 2.4 | 0.6 |
| 13203-19 | Calsicat E-144 SDU | 60 | 100 | 93.5 | 95.0 | 2.5 | 2.4 | 0.8 |
| 13203-14 | Calsicat E-144 SDU | 80 | 100 | 92.8 | 95.6 | 2.7 | 2.2 | 0.8 |
| 13203-23 | Calsicat E-144 SDU | 100 | 100 | 94.0 | 97.6 | 0.4 | 2.1 | 0.0 |
| 12560-3 | IFP LD-265 | 80 | 100 | 96.0 | 77.9 | 17.0 | 4.4 | — |
| 12560-1 | UCI G-68E | 80 | 96.8 | 91.4 | 68.2 | 21.7 | 4.3 | — |

Complete conversion of the isoprene ether and complete or very near complete conversion of the piperylene ethers are achieved with Calsicat E-144 SDU at temperatures as low as 40° C. The truly impressive aspect is the very high selectivities (95%) to the desired saturated piperylene ether achieved at only 60° C. At 40° C. the selectivity drops to 88% while the vinyl ethers increase to 14%. Apparently, at this mild temperature, the isomerization reaction, which results in vinyl ethers, can effectively compete with the desired hydrogenation reaction.

The superiority of Calsicat E-144 SDU, in terms of selectivity to the saturated piperylene ether over either IFP LD-265 or UCI G-68E, can also been seen from Table 2. Low selectivity to vinyl ethers is also very important because it is these compounds which, when in the presence of even trace amounts of water, will hydrolyze to give 2-pentanone. Although the IFP LD-265 catalyst did give selectivities of saturated piperylene ether as high as 94%, the conditions necessary to accomplish this were relatively much more severe, i.e., 100° C.; LHSV=1. Calsicat E-144 SDU's enhanced activity will allow operating at temperatures as low as 60° C. while still achieving high selectivity to the saturated piperylene ether.

The ability to operate at low temperature should significantly extend catalyst run length. This is because the rate of catalyst poisoning by sulfur containing compounds is known to be temperature dependent and also starting at low temperatures leaves more room to ramp up the temperature as the catalyst slowly deactivates.

The effect of space velocity upon Calsicat E-144 SDU performance was also investigated. All the runs shown below were at 80° C. and 300 psig.

TABLE 3

| Run No. | LHSV | Light Isoprene Ether Conv. | Piper. Ether Conv. | Selectivity | | | |
|---|---|---|---|---|---|---|---|
| | | | | Sat. Piper. Ether | Vinyl Ethers | 2-Pentanone | Ketal |
| 13023-11 | 1 | 100 | 94.1 | 98.3 | 0.5 | 0.6 | — |
| 13023-9 | 1.5 | 100 | 93.2 | 99.7 | 0.3 | 2.6 | — |
| 13023-14 | 2 | 100 | 92.8 | 95.6 | 2.7 | 2.2 | 0.8 |

Complete or near complete conversions of both isoprene and piperylene ethers are achieved at LHSV 1–3. Not surprisingly, at the higher space velocities the selectivity to vinyl ethers increases. This is because it is surmised that the vinyl ethers formed are not in contact with the catalyst surface long enough to be totally hydrogenated.

What is claimed is:

1. In a process for separating $C_4$ to $C_7$ tertiary mono-olefin(s) present in a $C_4$ to $C_7$ hydrocarbon mixture containing diolefins which comprises selectively reacting said tertiary mono-olefin mixture with a primary alcohol in the presence of an acid catalyst to convert the tertiary mono-olefin(s) to tertiary ether(s), separating the tertiary ether(s) from the unreacted hydrocarbon mixture to produce a tertiary ether(s) containing stream and contacting said tertiary ether(s) containing stream with a catalyst to decompose the tertiary ether(s) to tertiary olefin(s) and a primary alcohol, the improvement which comprises hydrogenating the tertiary ether(s) containing stream after that stream has been separated from the unreacted hydrocarbon mixture and prior to the decomposition step to saturate the unsaturated ether(s) formed from the diolefins present in the hydrocarbon mixture.

2. The process of claim 1 in which the tertiary mono-olefin is isobutylene and the primary alcohol is methanol.

3. The process of claim 1 in which the tertiary mono-olefin is isoamylene and the primary alcohol is methanol.

4. The process of claim 1 in which the hydrogenation catalyst is a Group VIII noble metal catalyst and the hydrogenation is carried out at a temperature of 40° C. to 200° C. in the present of 1.0 to 2.0 moles of $H_2$/mole of unsaturation present in the feed at a space velocity of 0.5 LHSV to 4.0 LHSV.

5. The process of claim 4 in which the hydrogenation catalyst is 0.1 to 1.0 weight percent of a Group VIII noble metal dispersed on alumina having a surface area of 1.0 to 200 $m^2$/gm.

6. The process of claim 4 in which the hydrogenation catalyst is a 0.5 weight percent Pd on alumina catalyst having a surface area of approximately 35 $m^2$/gm.

7. The process of claim 4 in which the tertiary ether containing stream to the hydrogenation step contains less than 1000 ppm water.

8. The process of claim 7 wherein the tertiary ether containing feed to the hydrogenation step contains less than 50 ppm water.

9. A process for the hydrogenation of unsaturated ethers in the presence of saturated ethers which comprises the steps of:

separating a mixed ether stream containing a minor amount of unsaturated ethers and a major amount of $C_4$ to $C_7$ saturated tertiary ethers from a stream containing $C_4$ to $C_7$ hydrocarbons, and contacting the mixed ether stream with a hydrogenation catalyst comprising 0.1 to 1.0 weight percent of a Group VIII noble metal dispersed on an alumina having a surface area of 1 to 200 $m^2$/gm, at a temperature of from 40° C. to 200° C., in the presence of 1.0 to 2.0 mols of $H_2$/mol of unsaturation present in the mixed ether stream, at a space velocity of 0.5 to 4.0 LHSV to saturate the $C_4$ to $C_7$ unsaturated ethers.

10. The process of claim 8 in which the hydrogenation step is carried out in the liquid phase in the presence of a catalyst comprising 0.5 weight percent Pd on alumina having a surface area of approximately 30 to 40 $m^2$/gm.

11. The process of claim 9 wherein the tertiary ether containing feed to the hydrogenation step contains less than 1000 ppm water.

12. The process of claim 11 wherein the tertiary ether containing feed to the hydrogenation step contains less than 50 ppm water.

* * * * *